(12) United States Patent
Genova et al.

(10) Patent No.: US 6,848,152 B2
(45) Date of Patent: Feb. 1, 2005

(54) METHOD OF FORMING BARBS ON A SUTURE AND APPARATUS FOR PERFORMING SAME

(75) Inventors: Perry Genova, Chapel Hill, NC (US); Robert C. Williams, III, Raleigh, NC (US); Warren Jewett, Cary, NC (US)

(73) Assignee: Quill Medical, Inc., Research Triangle Park, NC (US)

( * ) Notice: Subject to any disclaimer, the term of this patent is extended or adjusted under 35 U.S.C. 154(b) by 125 days.

(21) Appl. No.: 09/943,733

(22) Filed: Aug. 31, 2001

(65) Prior Publication Data

US 2003/0041426 A1 Mar. 6, 2003

(51) Int. Cl.$^7$ .............................................. B21F 25/00
(52) U.S. Cl. .................................................... 29/7.1
(58) Field of Search ........................... 29/7.1, 7.2, 7.3; 606/228, 215, 224, 216

(56) References Cited

U.S. PATENT DOCUMENTS

| | | |
|---|---|---|
| 2,355,907 A | 8/1944 | Cox |
| 2,572,936 A | 10/1951 | Kulp et al. |
| 2,866,256 A | 12/1958 | Matlin |
| 3,003,155 A | 10/1961 | Mielzynski et al. |
| 3,123,077 A | 3/1964 | Alcamo |
| 3,716,058 A | 2/1973 | Tanner, Jr. |
| 4,635,637 A | 1/1987 | Schreiber |
| 5,123,913 A | 6/1992 | Wilk et al. |
| 5,222,976 A | 6/1993 | Yoon |
| 5,269,783 A | 12/1993 | Sander |
| 5,342,376 A | 8/1994 | Ruff |
| 5,374,268 A | 12/1994 | Sander |
| 5,425,746 A | 6/1995 | Proto et al. |
| 5,425,747 A | 6/1995 | Brotz |
| 5,450,860 A | 9/1995 | O'Connor |
| 5,500,000 A | 3/1996 | Feagin et al. |
| 5,584,859 A | 12/1996 | Brotz |
| 5,931,855 A * | 8/1999 | Buncke ...................... 606/228 |
| 6,241,747 B1 | 6/2001 | Ruff |
| 6,443,962 B1 | 9/2002 | Gaber |
| 2003/0149447 A1 | 8/2003 | Morency et al. |

FOREIGN PATENT DOCUMENTS

| | | |
|---|---|---|
| DE | 1 810 800 | 11/1968 |
| EP | 0 576 337 A1 | 6/1993 |
| EP | 1 075 843 A1 | 2/2001 |
| WO | WO 00/51658 | 9/2000 |

OTHER PUBLICATIONS

A.R. McKenzie, "An Experimental Multiple Barbed Suture for the Long Flexor Tendons of the Palm and Fingers; Preliminary Report"; *The journal of Bone and Joint Surgery*, vol. 49 B, No. 3, Aug. 1967, pp. 440–447.

Sulamanidze, M.A.; Shiffman, M.A.; Paikidze, T.G.; Sulamanidze, G.M.; Gavasheli, L.G.; "Facial Lifting with APTOS Threads", *International Journal of Cosmetic Surgery and Aesthetic Dermatology*, No. 4 2001.

* cited by examiner

Primary Examiner—John C. Hong
(74) Attorney, Agent, or Firm—Frommer Lawrence & Haug LLP; Ronald R. Santucci

(57) ABSTRACT

A method of making a barbed suture by varying the blade geometry and/or the movement of the blade when cutting a suture. The method can also be accomplished with a cutting device to create a plurality of barbs on the exterior of surgical suture. The barbs produced using the method with the cutting device can be the same or random configurations.

29 Claims, 19 Drawing Sheets

TOP

SIDE

METHOD OF FORMING BARBS ON A SUTURE AND APPARATUS FOR PERFORMING SAME

BACKGROUND OF THE INVENTION

1. Field of the Invention

The invention relates to a method of barbing suture filament by varying the blade geometry and/or the movement of a blade when cutting a suture filament where the method can also be utilized to cut a plurality of axially spaced barbs on the exterior of sutures and an apparatus for performing this.

2. Description of the Prior Art

In the prior art, it is well known that surgical and traumatic wounds are typically closed with a filament introduced into the tissue by a needle attached to one end. Closure of the wound and holding tissues together supports healing and re-growth. What is typically used for this procedure is known as a suture.

A barbed suture is a one-way suture which allows passage of a needle-drawn suture in one direction through tissue, but not in the opposite direction. A barbed suture is generally an elongated body having a pointed leading end and a plurality of axially and circumferentially spaced barbs on the exterior surface of the elongated body.

In closing a wound with a barbed suture, the suture is passed through tissue at each of the opposed sides of a wound. Suture pairs are formed in which trailing ends of sutures are positioned generally in alignment at opposite sides of the wound. On insertion of each suture, the needle is pushed to extend out of the tissue at a point laterally remote from the wound, then the needle is pulled out to draw the suture to the desired position, and the suture is then severed from the needle. (Note that methods of using barbed sutures are disclosed in copending U.S. patent application Ser. No. 09/896,455, filed Jun. 29, 2001 entitled "Suture Method", and is assigned to Quill Medical, Inc., the disclosure of which is incorporated herein by reference.) The advantage of using barbed sutures is that there is an ability to put tension in the tissue with the result of less slippage of the suture in the wound. The number of suture pairs is selected in accordance with the size of the wound and the strength required to hold the wound closed. Although tissue anchoring is easier done with a very pointed barb and a relatively skinny tip, better tissue holding results are obtained with a fuller tip barb.

In some circumstances of tissue repair, a random configuration of barbs on the exterior of the suture might be preferred. With as many barb angles as possible, superior wound holding would be achieved. However, in other circumstances where the wound or tissue repair needed is small, a small suture would be preferable. A small suture would require a reduced number of barbs on the exterior of the suture.

Various methods of cutting the barbs have been proposed (see i.e. U.S. Pat. No. 5,931,855). However, such methods have not been commercially exploited for reasons which are unclear.

It is seen from the foregoing that there is a need for a method of cutting barbs on the exterior of sutures with a minimum of difficulty and in a reliable and relatively economic fashion so as to allow for the wide spread commercialization of such sutures. Such a method should also be able to vary the size of the barbs, their location and depth to allow for variation thereof and virtuality of their application. The method should be able to cut a plurality of barbs with the positioning depending on the number of barbs needed. The need also exists for a device able to use the method described above which can provide a plurality of axially spaced barbs either in a random or similar configuration, with the configuration depending upon, among other things, the type of tissue being repaired.

SUMMARY OF THE INVENTION

It is therefore a principal object of the present invention to provide for a practical method of cutting barbs in a suture.

It is therefore a further object of the present invention to provide a method for cutting fuller tipped barbs of various sizes on the exterior of a suture.

It is therefore a still further object of the present invention to provide a method for cutting a plurality of axially spaced barbs on the exterior of a suture.

It is therefore a still further object of the present invention to provide a method for cutting a plurality of axially spaced barbs circumferentially about the exterior of a suture.

It is therefore a still further object of the present invention to provide a method for cutting a plurality of axially spaced barbs in similar or random configurations on the exterior of a suture.

It is therefore a yet further object of the invention to provide for an illustrative apparatus to perform this method.

To attain the objects described, there is provided a cutting method which produces suture barbs of varying sizes depending on the geometry of the blade being used and/or the movement of the blade when cutting into a suture. By altering the blade geometry or degree of blade movement, the barbs can be made of varying sizes designed for various surgical applications. For example: for joining fat and relatively soft tissues, larger barbs are desired, whereas smaller barbs are more suited for collagen intensive tissues. Also, the use of a combination of large and small barbs on the same suture will ensure maximum anchoring properties wherein barb sizes are customized for each tissue layer.

The cutting method may be achieved with a cutting device disclosed herein. The device disclosed can produce six sets of barbs in staggered positions along the length of the suture, such that three sets of barbs are faced opposite to another three sets of barbs. Viewing the suture on a cross-sectional plane, the barb sets would be positioned either 120 or 180 degrees to each other, depending on the cutting method. Longitudinally, each barb cut would begin where the nearest one ends.

Compared with the method of cutting barbs in an untwisted state, using the twisted configuration can: simplify production equipment; produce a stronger suture; reduce production cycle time by at least a factor of three; and be easily scalable to smaller diameters and produces barbs in a spiral fashion rather than at 120 or 180 degrees.

By way of variations, slight modifications, and/or combinations of the methods of cutting with and without twisting the suture, barbs can be obtained with random configurations. There are instances in tissue repair that the random configuration may be ideal to anchor tissues in as many barb angles as possible to provide superior wound holding properties. These and other objects and characteristics of the present invention will become apparent from the further disclosure to be made in the detailed description given below.

BRIEF DESCRIPTION OF THE DRAWINGS

Thus by the present invention its objects and advantages will be realized the description of which should be taken in conjunction with the drawings wherein.

DETAILED DESCRIPTION OF THE PREFERRED EMBODIMENT

We refer now to the drawings in detail wherein like numerals refer to like elements throughout the several views.

The purpose of the present invention is to provide for an effective way of producing a barbed suture. In this regard, several different types of methods are disclosed which are directed to the cutting action of a blade on the suture to create the barbs. As will be described, the cutting action envisioned takes into account the movement of the blade and the blade geometry.

Essentially, the cutting of the suture with a blade takes into account three dimensions x-y-z of the suture 6. Each dimension is important and may be addressed by the cutting motion of the blade and/or the blade geometry. Depending on the blade geometry, the blade movement can have an effect in the other dimensions.

Figure 1A:
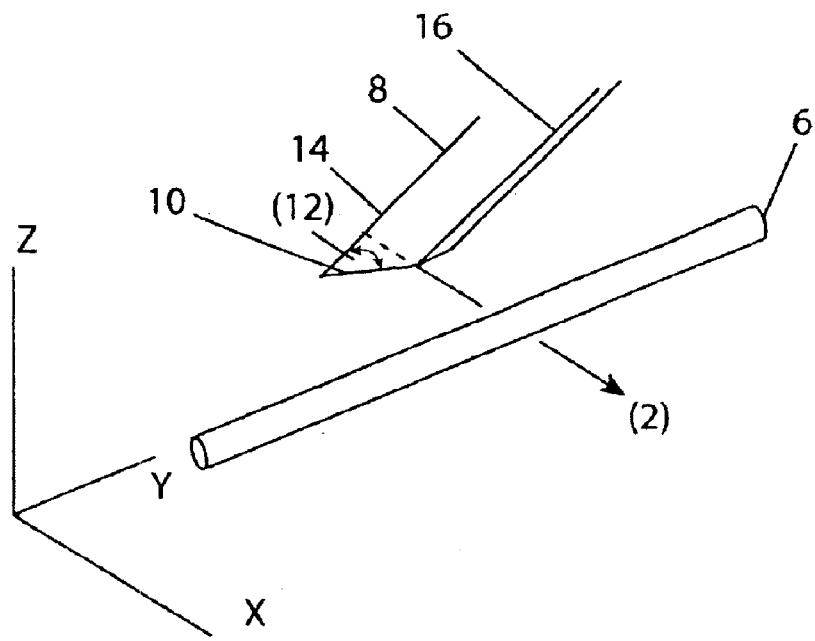
FIGS. 1A–C depict the cutting motion of a blade with one degree of freedom from movement and two degrees of freedom from blade geometry.

In this regard FIG. 1A illustrates a consistent cutting motion of a blade 8 with one degree of freedom of movement and two degrees of freedom from blade geometry across a suture 6. One degree of freedom from movement is movement in one direction in a three-dimensional "x-y-z" layout. For FIG. 1A, direction 2 follows the lateral "x" axis in the cut of suture 6, with the movement of blade 8 in direction 2 before accomplishing a cut. An edge 10 of blade 8 would have an angle, depicted as (12), in its blade geometry between the tips of sides 14, 16 of blade 8. Such a geometry will cause an effect in the y and z dimensions just by the movement in the x direction.

Figure 1B:
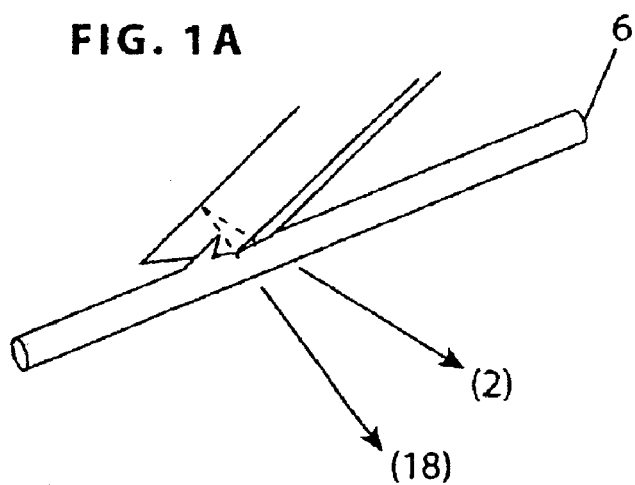
Figure 1C:
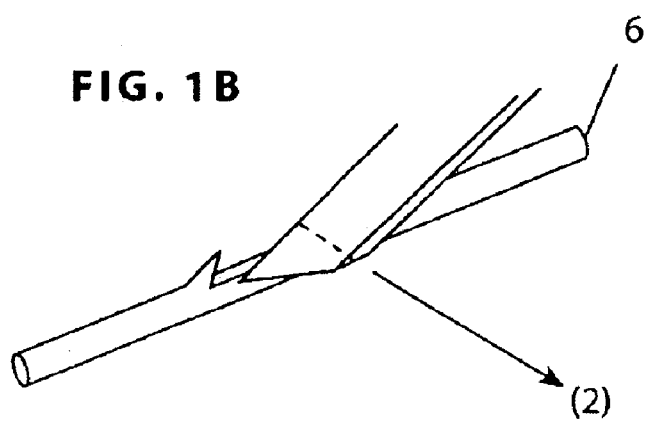

As shown in FIG. 1B, angle (12) allows a cut into suture 6 during movement in direction 2. This cutting-into movement is depicted as direction 18. FIG. 1C depicts the completed cut of suture 6 with a continued movement in direction 2 away from the suture 6.

Figure 2A:
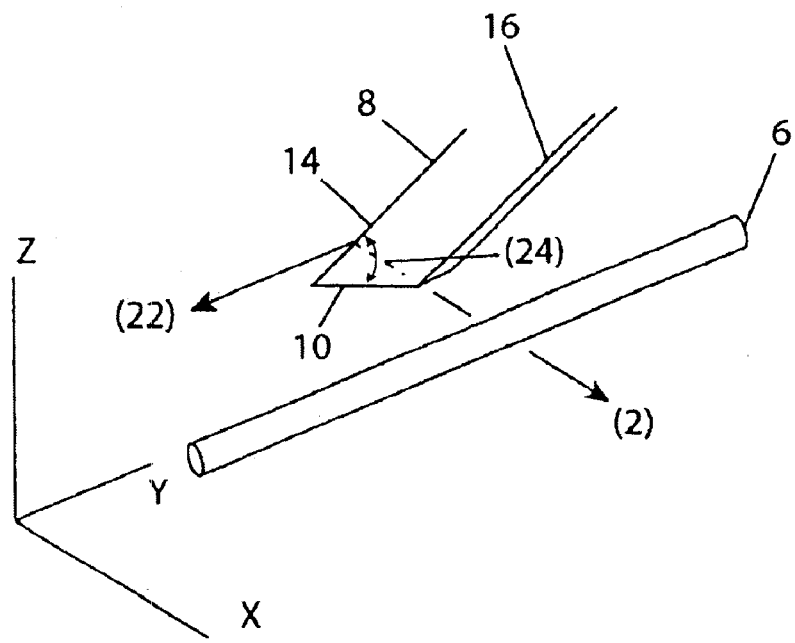
FIGS. 2A–C depict the cutting motion of a blade with two degrees of freedom from blade movement and one degree of freedom from blade geometry.
Figure 2B:
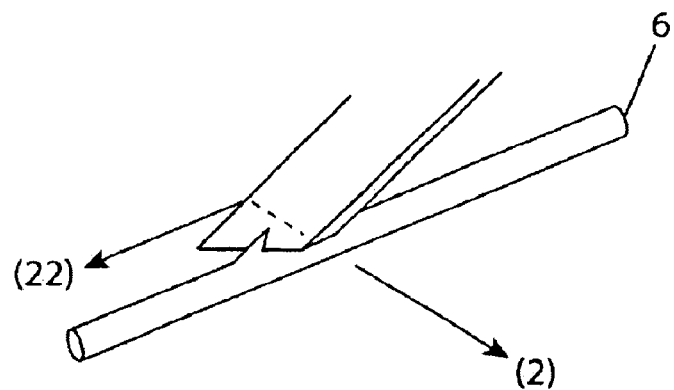
Figure 2C:
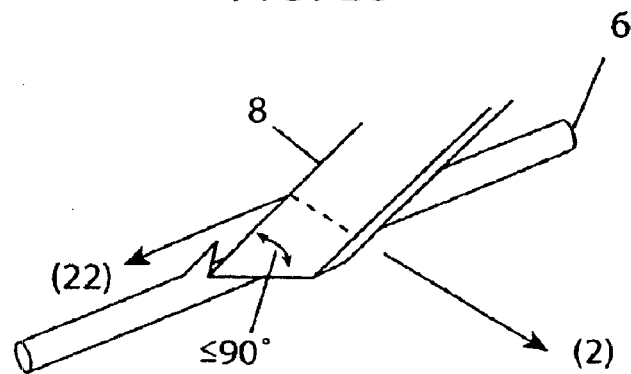

Turning now to FIGS. 2A–C, they illustrate a consistent cutting motion of a blade with two degrees of freedom of movement and one degree of freedom from blade geometry. Two degrees of freedom of movement is movement in two directions x and y. For FIG. 2A, direction 2 follows the lateral "x" axis and direction 22 follows the forward "y" axis in the cut of suture 6. In this regard the movement of blade 8 is necessary in two directions 2 and 22 before accomplishing a cut. Edge 10 of blade 8 is at an angle of 90° or less, depicted as (24), of one degree in its blade geometry between the tips of sides 14, 16 of blade 8.

As shown in FIG. 2B, forward movement in direction 22 and along a lateral direction 2 allows a deeper cut into suture 6 than produced in FIG. 1, since in FIG. 1 the blade geometry determines the depth of the barb, whereas in FIG. 2 the blade movement along the "y" and "x" axis determines the depth of the barb. This deeper cutting action is in the z direction. FIG. 2C shows the completed cut of the suture 6 with a continued movement in direction 2 away from the suture.

Figure 3A:
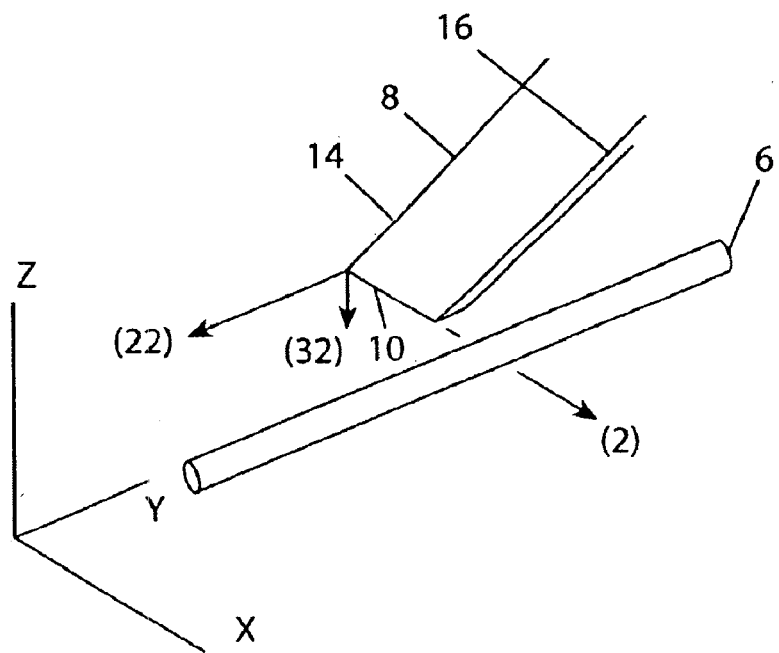
FIGS. 3A–C depict the cutting motion of a blade with three degrees of freedom from blade movement and a solid plane geometry.
Figure 3B:
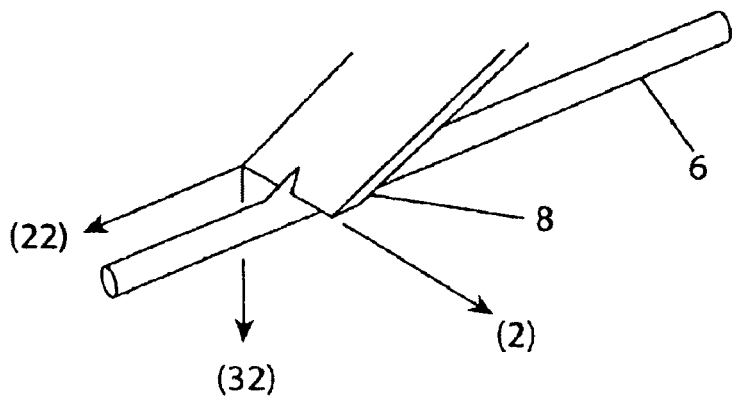

FIG. 3A illustrates a further consistent cutting motion of a blade with three degrees of freedom of blade movement and edge 10 of 90° or less. Three degrees of freedom from movement is movement in the three directions of a three-dimensional "x-y-z" layout. For FIG. 3A, direction 2 follows the lateral "x" axis, direction 22 follows the forward "y" axis and direction 32 follows the downward "z" axis. The movement of blade 8 in all three directions 2, 22 and 32 is necessary to accomplish the cutting of a barb on the suture 6.

Figure 3C:
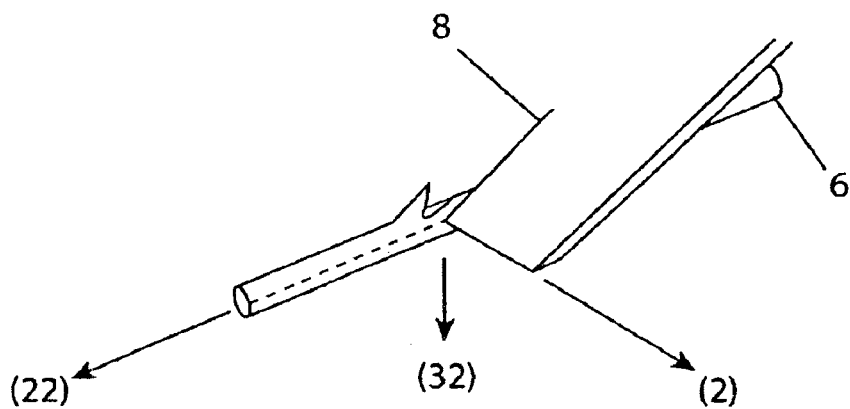

The combination of movement in lateral direction 2, forward direction 22 and downward direction 32 would allow one to vary the depth of the cut to create a barb. It may be a deeper cut by cutting further in direction 32. FIG. 3C shows the completed cut of suture 6 with a continued movement in direction 2, 22 and 32 away from the suture 6.

Figure 4A:
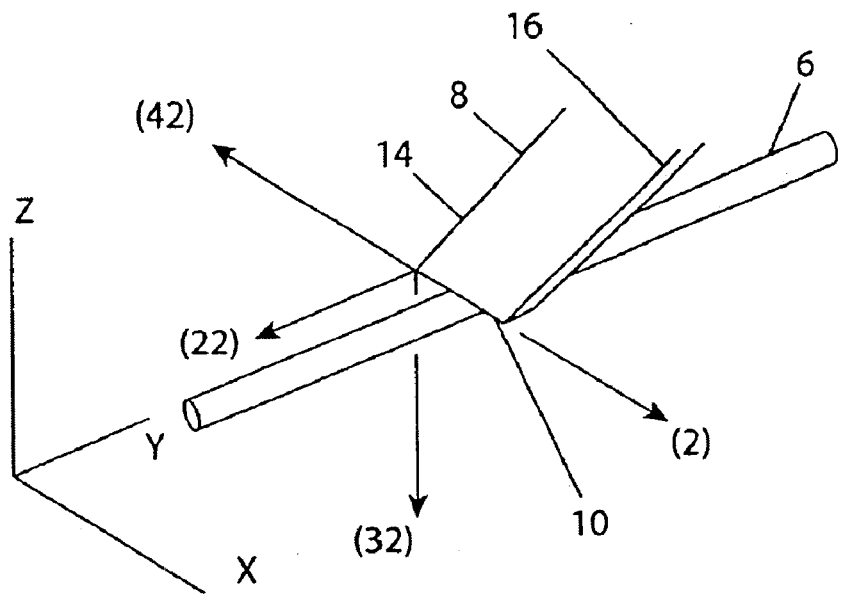
FIGS. 4A–C depict a zigzag (oscillating back and forth and downward) cutting motion of a blade with three degrees of freedom from blade movement and a solid plane blade geometry.
Figure 4B:
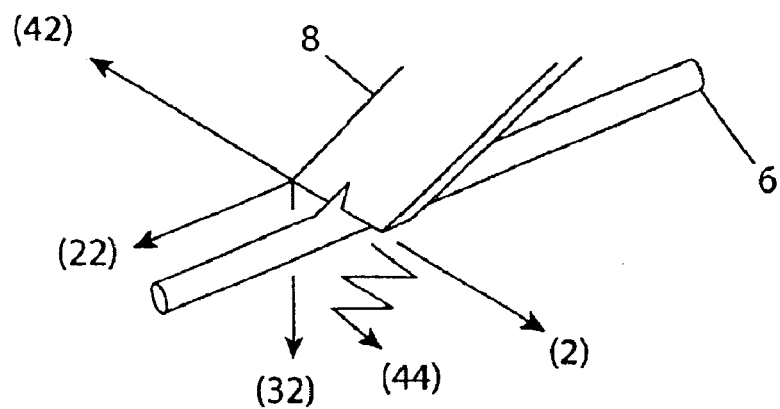
Figure 4C:
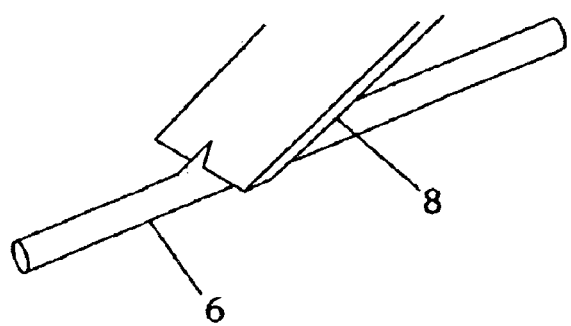

A yet further method of cutting a barb is shown in FIGS. 4A–C where a back and forth or zigzag (oscillating on the "x" axis combined with the movement in z or y axis) cutting motion of the blade with three degrees of freedom of blade movement, a solid plane geometry shown having a saw-like cutting motion. Three degrees of freedom of movement is movement in three directions in the three-dimensional "x-y-z" layout. In FIG. 4A, direction 2 follows the lateral "x" axis, direction 22 follows the forward "y" axis, direction 32 follows the downward "z" axis, and direction 42 follows the lateral "x" axis except in a direction opposite to direction 2.

FIG. 4A shows the movement necessary before accomplishing a cut of blade 8 in directions 22 and 32 with alternation in movement between directions 2 and 42. Edge 10 of blade 8 would be straight between the tips of sides 14, 16 of blade 8.

The combination of alternating movement in lateral directions 2 and 42, steady movement in forward direction 22 and steady movement in downward direction 32 allows the depth of the cut to be varied. The cutting depth is shown as alternating direction 44 in FIG. 4B. FIG. 4C shows the completed cut of suture 6.

The blade motion shown in FIGS. 1–4 can cut a suture filament made of polyglycolide, polydioxinone, polypropylene, other resorbables, other nonresorbables, Gore-Tex®, bi-component material or sutures made of other material suitable for the purpose.

While in the aforesaid examples, only a single blade is shown, it is envisioned that a plurality of blades may be utilized. They may be in tandem or on a rotary mechanism or on any other type of mechanical device which effects the implementation of the movement so described. Also, while the suture is shown in an untwisted state, it may be cut in a twisted state as hereinafter described.

By way of an example of a mechanical device for implementing the foregoing, reference is made to FIGS. 5–18. It should be understood, however, that this device should not be considered exclusive and other types of devices for such implementation are contemplated.

Figure 5:
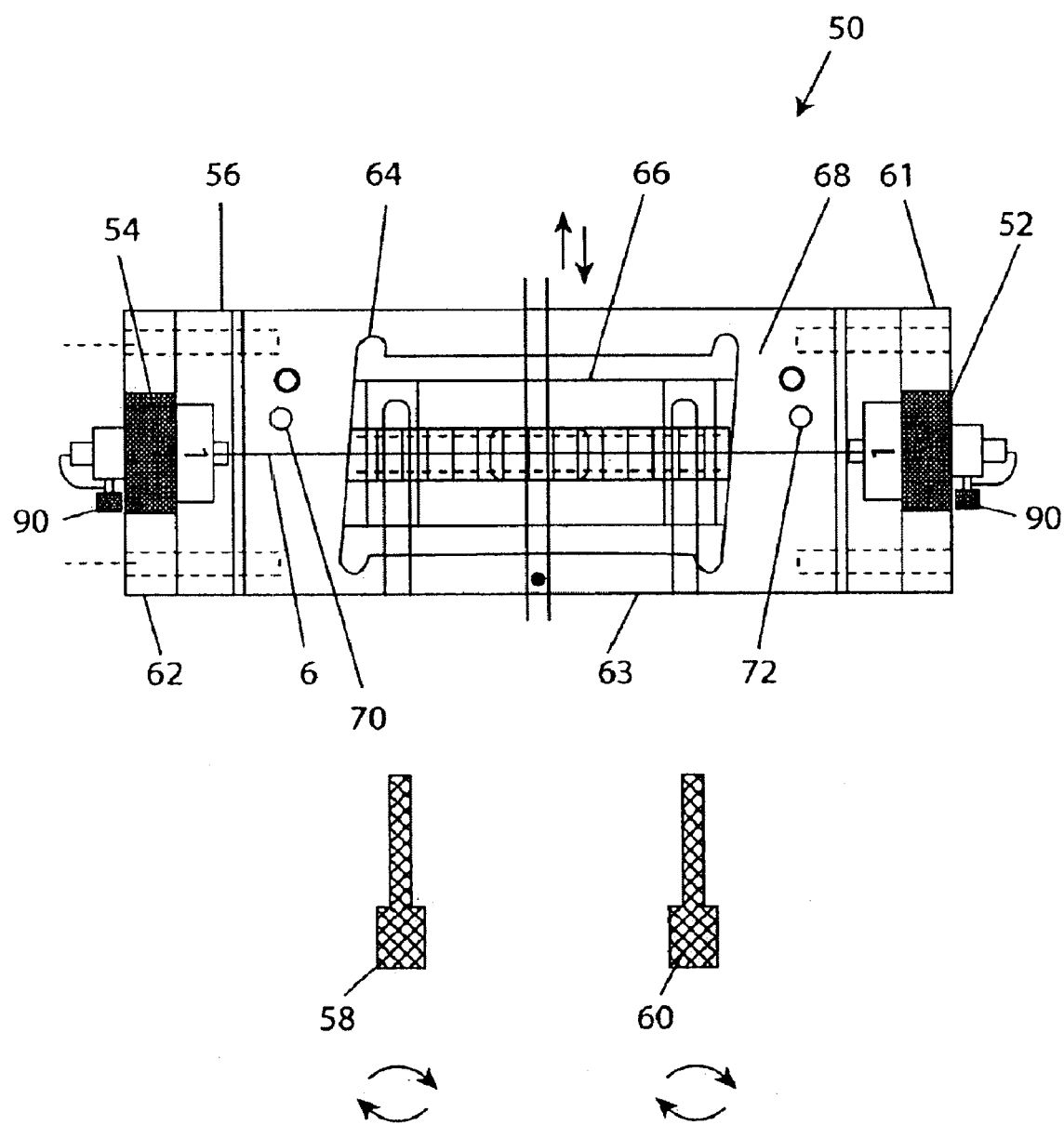
FIG. 5 is a top view of the assembled cutting device.
Figure 6:
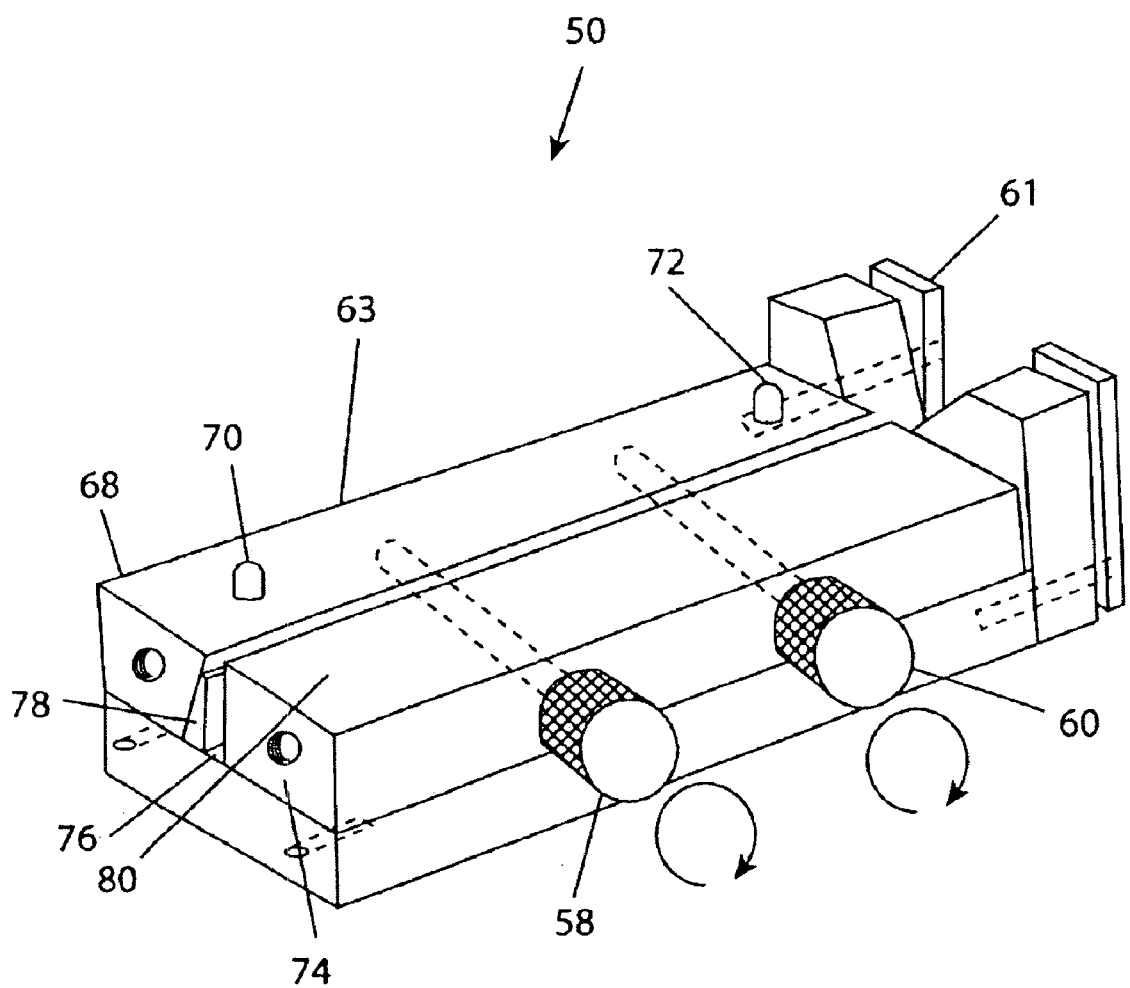
FIG. 6 is a perspective view of the cutting bed.

Turning now more particularly to FIG. 5, there is shown a cutting device 50 that allows an operator to cut multiple barbs on the exterior of suture 6 using the methods previously described. The cutting device 50 includes retention knobs 52, 54 for retaining the suture 6 on a vise 63 during cutting. Retention knobs 52, 54 include knob holders 61, 62. Cutting bed vise screws 58, 60 are used to open and to close cutting bed vise 63, where suture 6 is placed during cutting.

A cutting template 64 directs the cutting motion of a blade assembly 66 containing a plurality of blades across suture 6. Two additional cutting templates are provided for operation of the cutting device but are offset to provide a different axial position of the blades with respect to suture 6. The cutting templates have the same configuration as cutting template 64 and are installed in a similar manner throughout the several views. Also, while the templates shown are particularly suited for practicing one way of cutting the barbs, such templates can be readily modified to allow the performance of other ways, including those previously described as will be appreciated by a skilled artisan.

Cutting bed vise 63 assists in the alignment of the cutting templates. On the top of block 68 of cutting bed vise 63 are two protrusions. These protrusions are alignment pins 70, 72 which are used for setting the cutting templates and a tamp 101.

As will be apparent to one skilled in the art, the configuration of cutting bed vise 63 may vary. If the suture is rotated (e.g. 120 degrees or 180 degrees) to effect cutting barbs about its circumference, the cutting bed vise would take on the configuration shown in FIG. 5. If the suture is twisted prior to cutting, as will be discussed, the cutting bed vise 63 would have the configuration shown in FIG. 6. Note that the vise shown in FIG. 6 can also be used with a rotated suture, since there is a space to accommodate a cut barb. In this regard, in FIG. 6, blocks 68, 74 taper outward from the tops on their interior sides to a surface 76, with the blocks depicting a trapezoidal shape when viewed from an end profile. Protruding from the taper of block 68 is a trapezoidal or anvil suture clamp 78 which is used to secure suture 6 during the closing of cutting bed vise 63. Suture clamp 78 is a wedge shape which sets on surface 76 and ends slightly below top 80.

Figure 7:
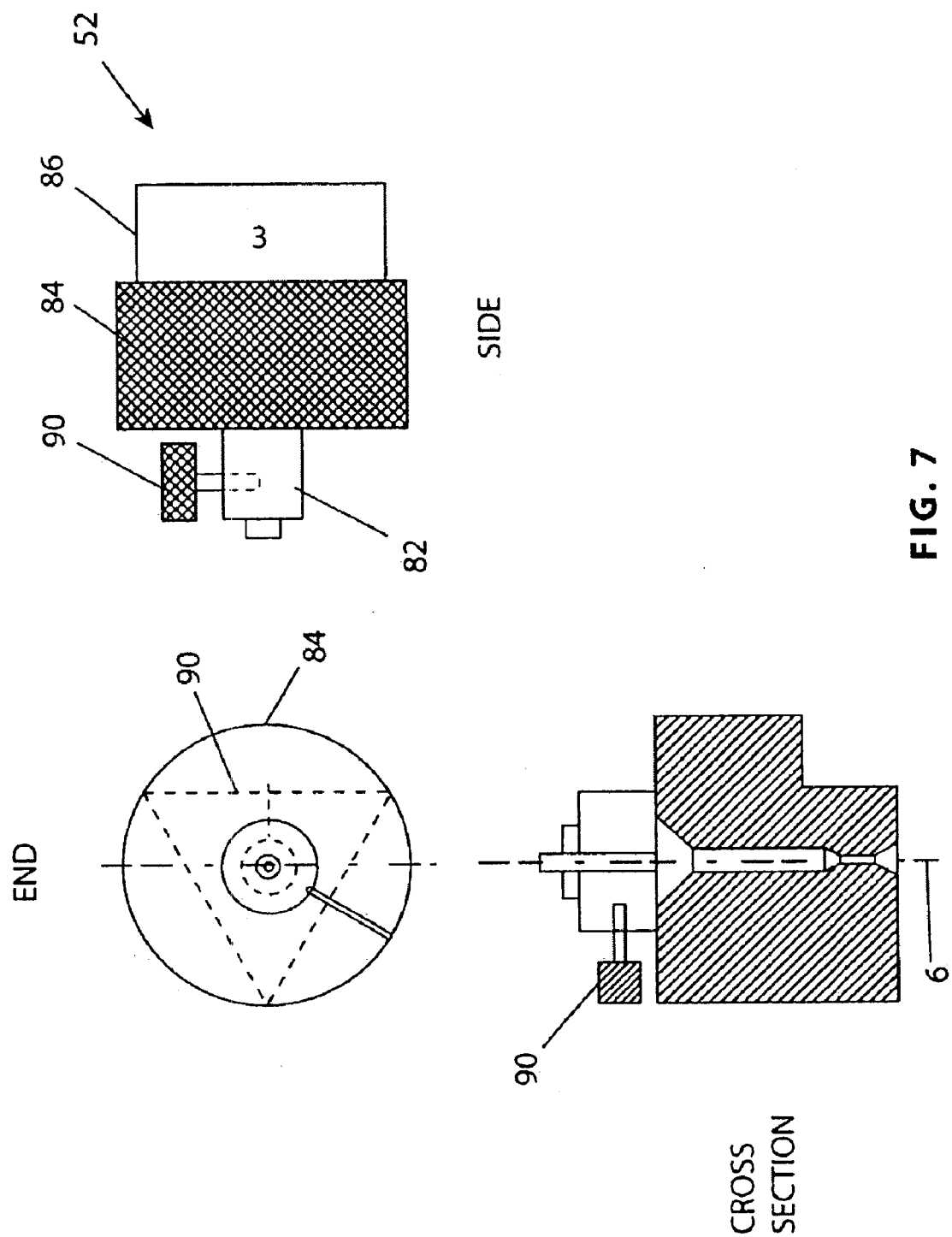
FIG. 7 depicts an end, a side, and a cross-sectional view of the retention knob of the cutting device.

In addition to securing suture 6, retention knobs 52, 54 are rotated between the various cutting methods and are numerically indexed for precise movement. As depicted in FIG. 7, retention knob 52 is a solid elongated body. Retention knob 52 comprises a cylinder 82 having a gripping area 84 integral with a triangular protrusion 86. Triangular protrusion 86 can rest on cutting bed 56 or a spacing bar 100, shown in FIG. 12. An anchor screw 90 secures suture 6 to the retention knob. The triangular protrusion includes numerical marks for guiding the operator in positioning the retention knob during various stages of the cutting method; however, the triangular protrusion may be indexed in other variations. One side of the triangular protrusion has the number "1" imprinted, another side has the number "2" imprinted and a third side has the number "3" imprinted. Retention knob 54, not shown, has the same characteristics as retention knob 52.

Figure 8:
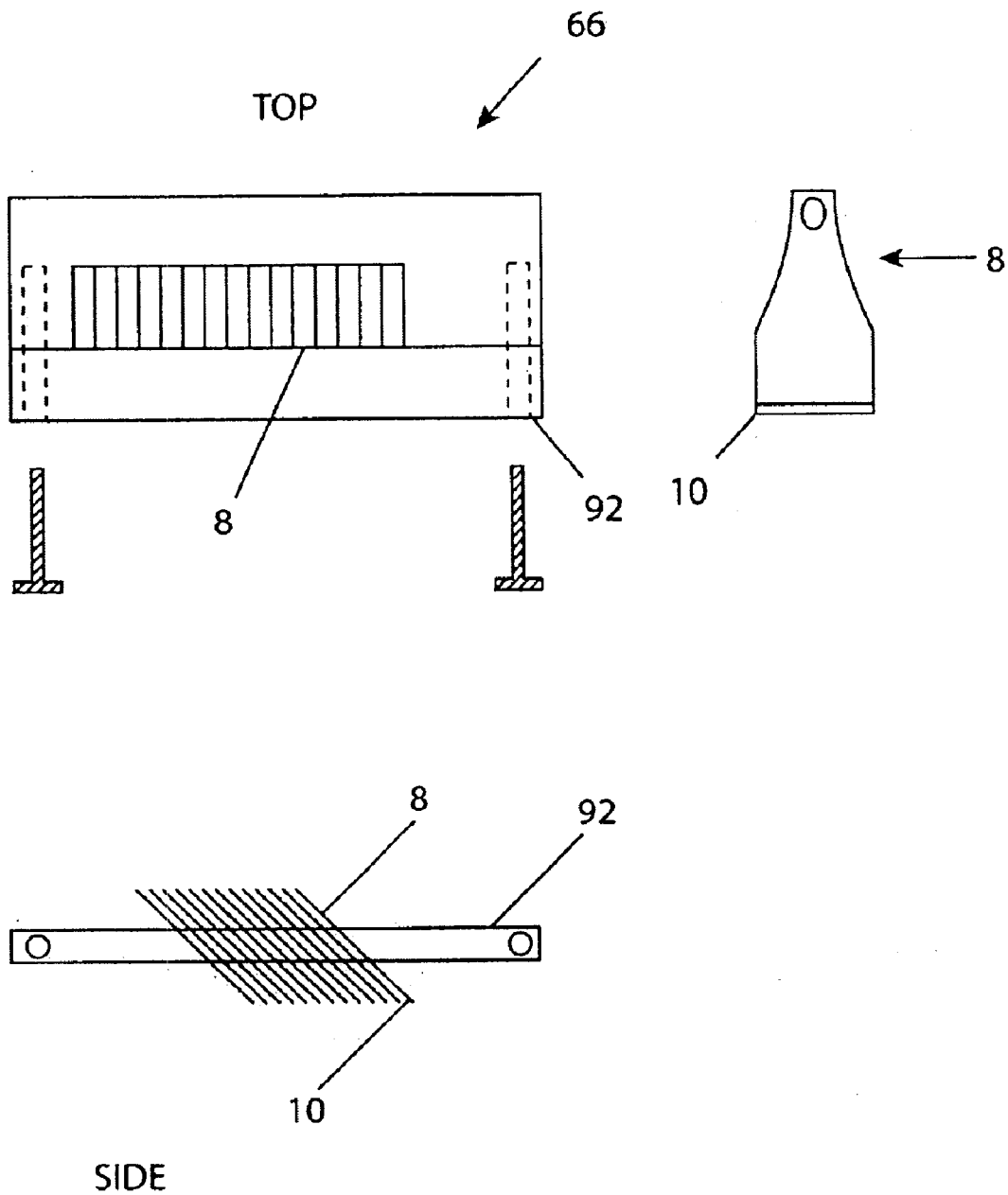
FIG. 8 depicts a top and side view of the blade assembly of the cutting device and a top view of an example blade for the blade assembly.
Figure 9:
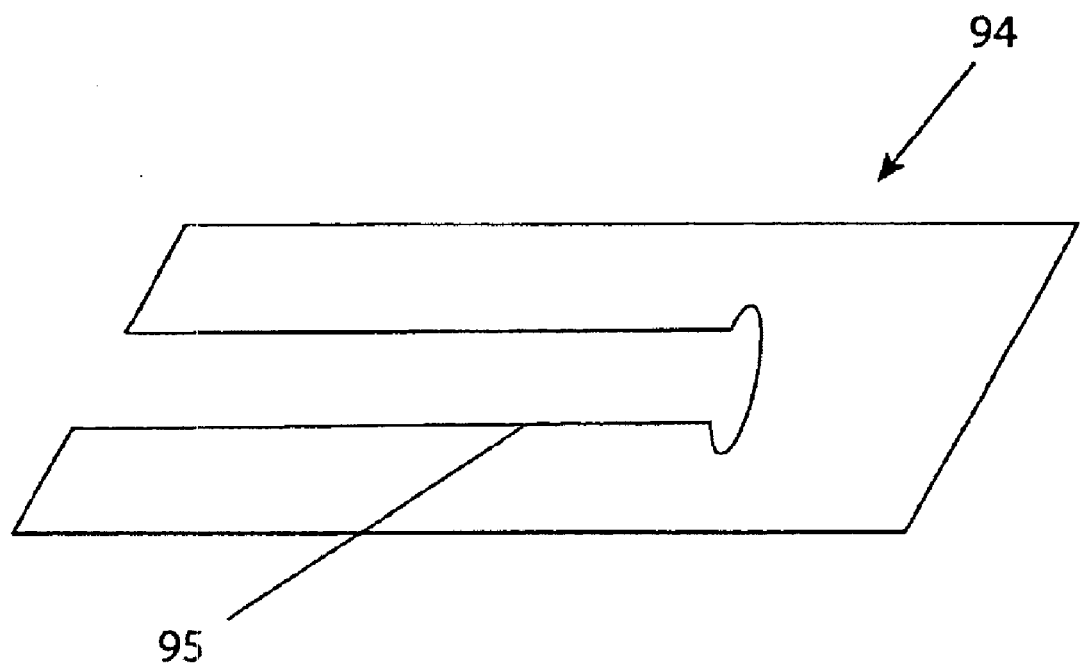
FIG. 9 depicts a top and side view of the template block of the blade assembly.
Figure 9:

For cutting a plurality of barbed sutures at one time, a multi-blade assembly is used. As depicted in FIG. 8, blade assembly 66 consists of thirteen blades (8) secured in retaining block 92. Obviously, the number of blades used may vary. Edge 10 of each of the blades used in the blade assembly would extend through a template block 94, shown in FIG. 9 by the amount of the desired barb depth.

Retaining block 92 of FIG. 8 consists of two rectangular blocks which retain blade assembly 66 by a vise action. Blade assembly 66 conformingly fits to a cutaway section of the retaining block and blades 8 are inserted at a desired angle, which in this case is 148 degrees. The blades are secured in the blocks 92 with the template block 94 attached thereto. Template block 94 acts as a guide for the blade assembly within the confines of the cutting templates.

Figure 10:
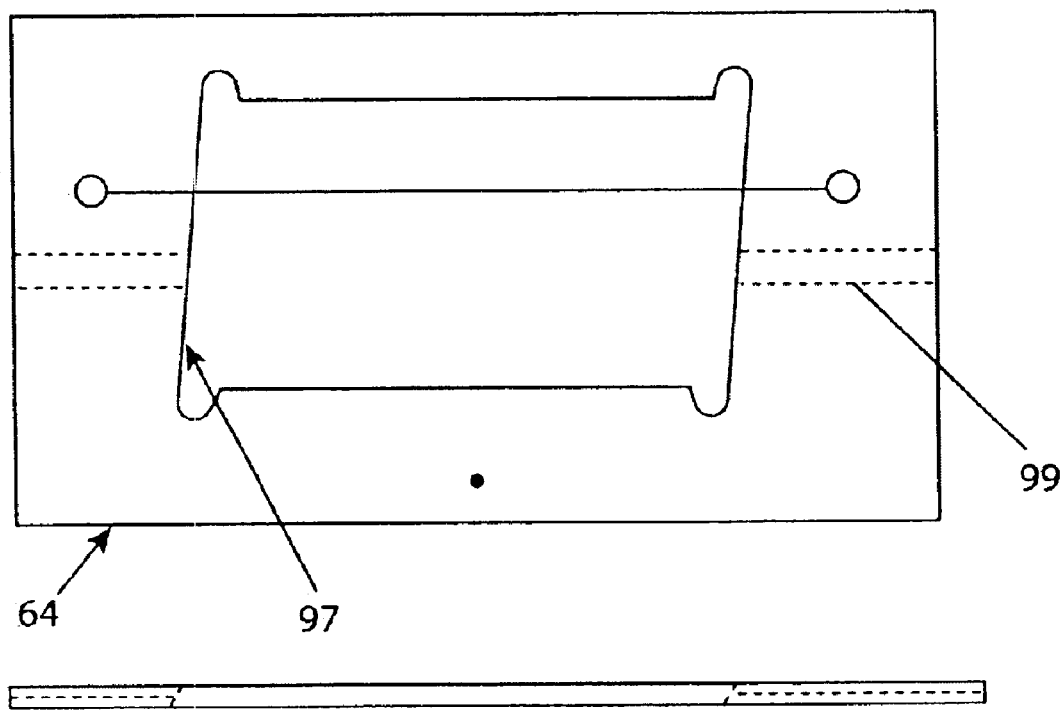
FIG. 10 depicts a top and side view of the cutting template used with the cutting device.

As shown in FIG. 10, the cutting template 64 provides a cutting path 97 for blade assembly 66. Cutting path 97 is shown as a parallelogram perimeter. Note, however, for example, the cutting path 97 may be shaped with a rectangular perimeter to suit the movements described in the cutting method of FIG. 1. Additional cutting templates are provided and are similarly made with the purpose of offsetting the blade cut in an axial direction. The cutting template 64 is identified so as to indicate to the user which one is to be used at which stage of cutting. On opposite sides of the cutting template 64 is a channel 99 sized to accommodate the other sections of suture 6 not being cut by blade assembly 66.

Figure 11A:
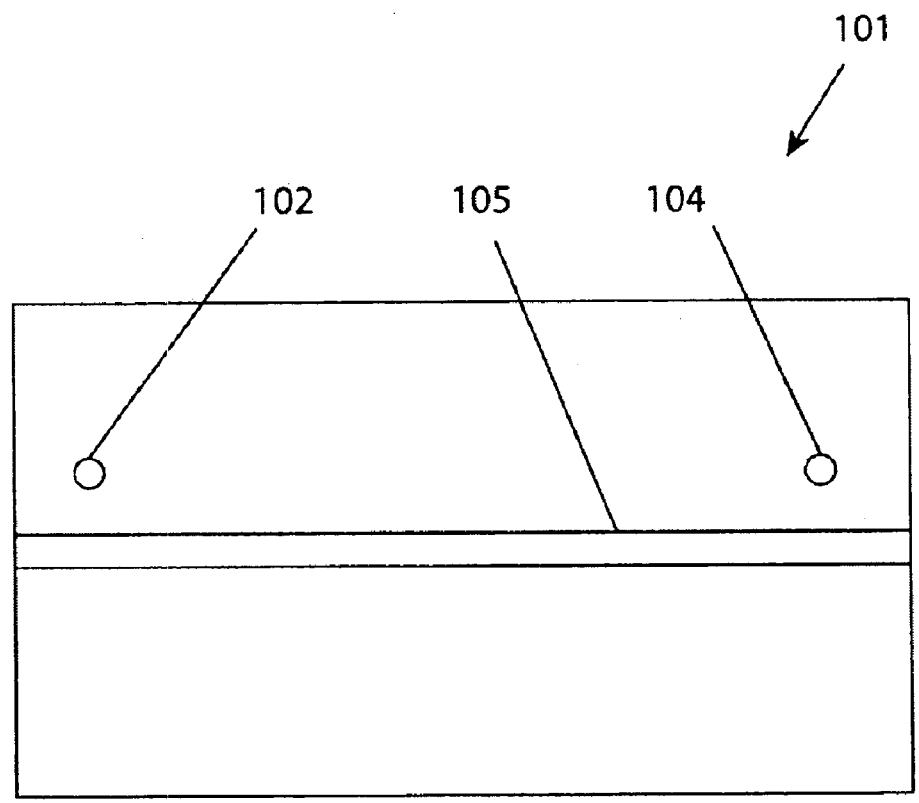
FIG. 11 depicts a top and side view of the tamp used with the cutting device.
Figure 11B:
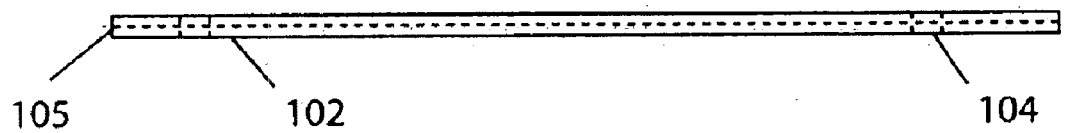

As shown in FIG. 11A, a tamp 101 is provided and allows the user to insure that suture 6 is uniformly seated on the anvil 78. Apertures 102, 104 on tamp 101 are provided to engage the alignment pins 70, 72. A channel 105 is provided to hold suture 6 in place during the calibration. The depth of the channel 105 equals the thickness of the suture 6 above top 80.

Figure 12:
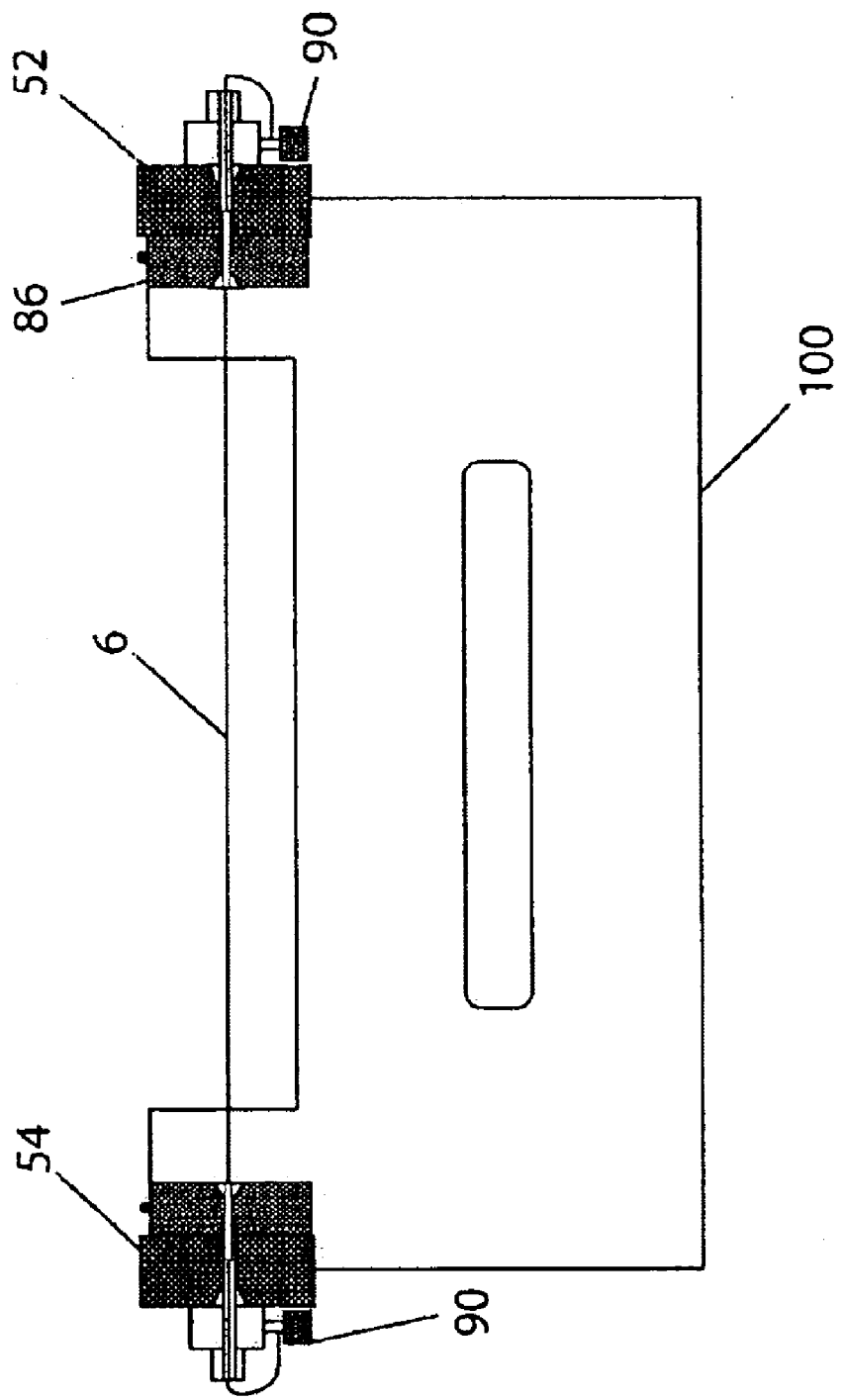
FIG. 12 depicts the securing of the suture to the retention knob and placement on the spacing bar.

To operate cutting device 50, first, one secures the suture 6 to anchor screws 90 on one of retention knobs 52, 54 as shown in FIG. 12.

Retention knob 52 is placed on the ledge of spacing bar 100 with the suture 6 drawn thereacross with the second retention knob 54 positioned on the opposing ledge. The suture should not be overly taut once it is secured to the second retention knob by anchor screw 90. After sizing, suture 6 is placed on cutting bed 56 and held in place by cutting bed vise 63. The retention knobs 52 and 54 are indexed in a first position. As will be apparent in a second and third cutting, they are rotated to a second and third position respectively.

Figure 13:
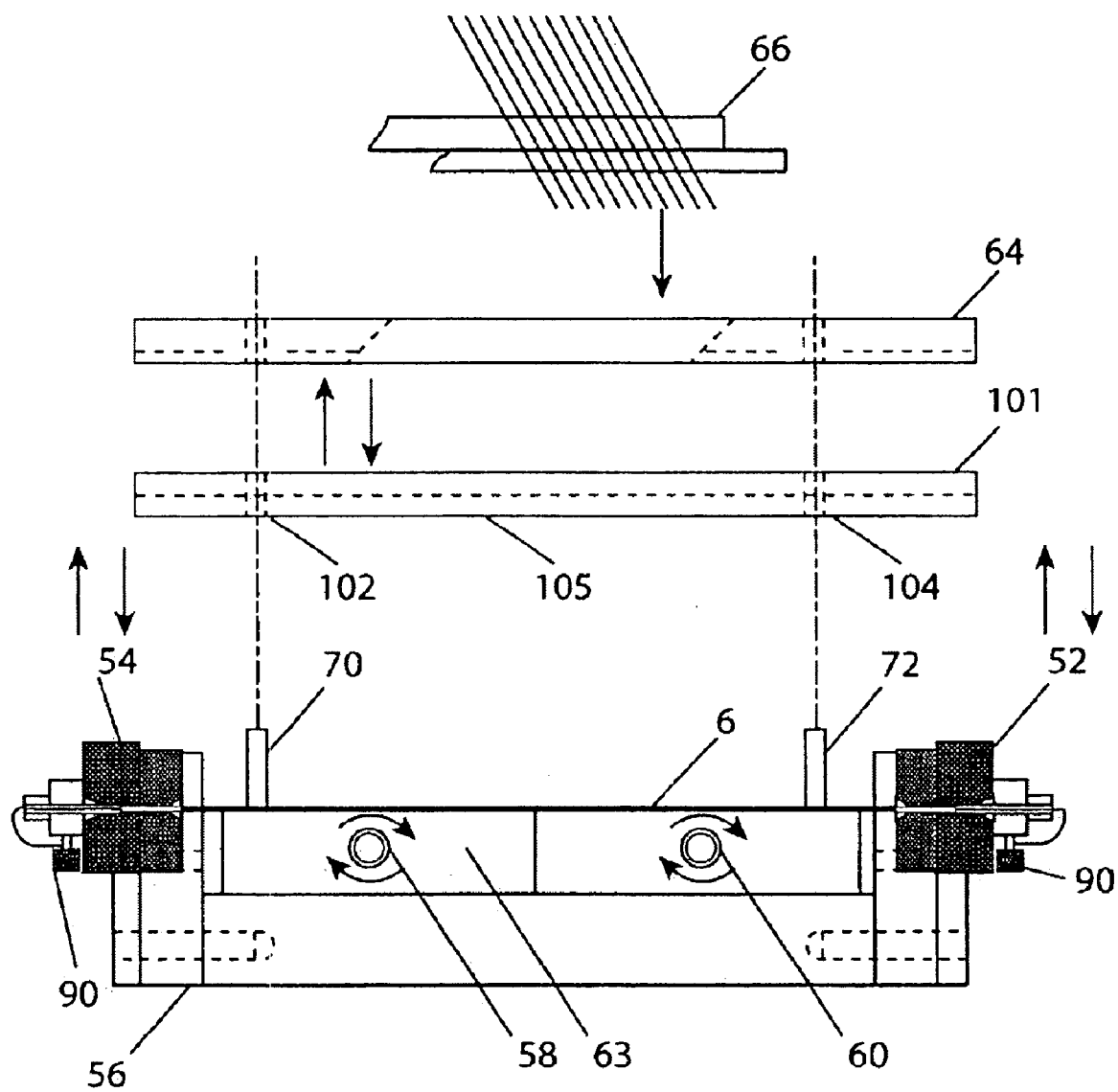
FIG. 13 depicts the placement of the various fixtures used with the cutting bed vise.
Figure 14:
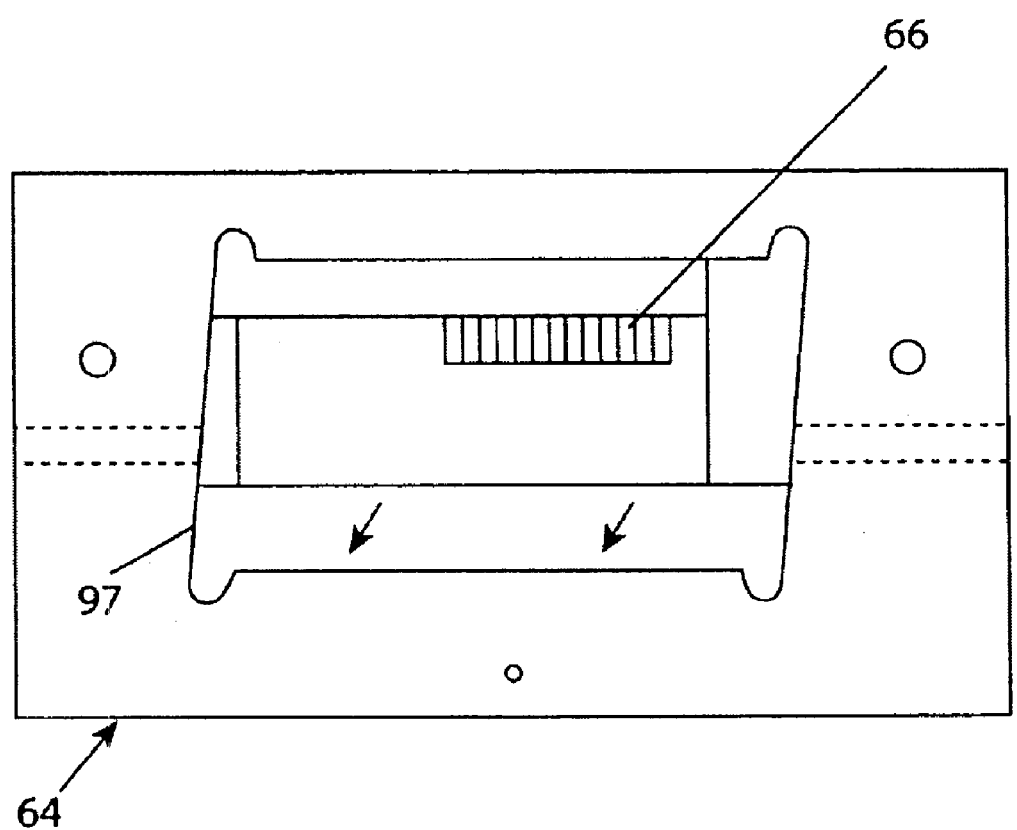
FIG. 14 depicts the blade assembly placement and downward movement in relation to the cutting template with the rest of the cutting device removed from the figure for clarity purposes.
Figure 15:
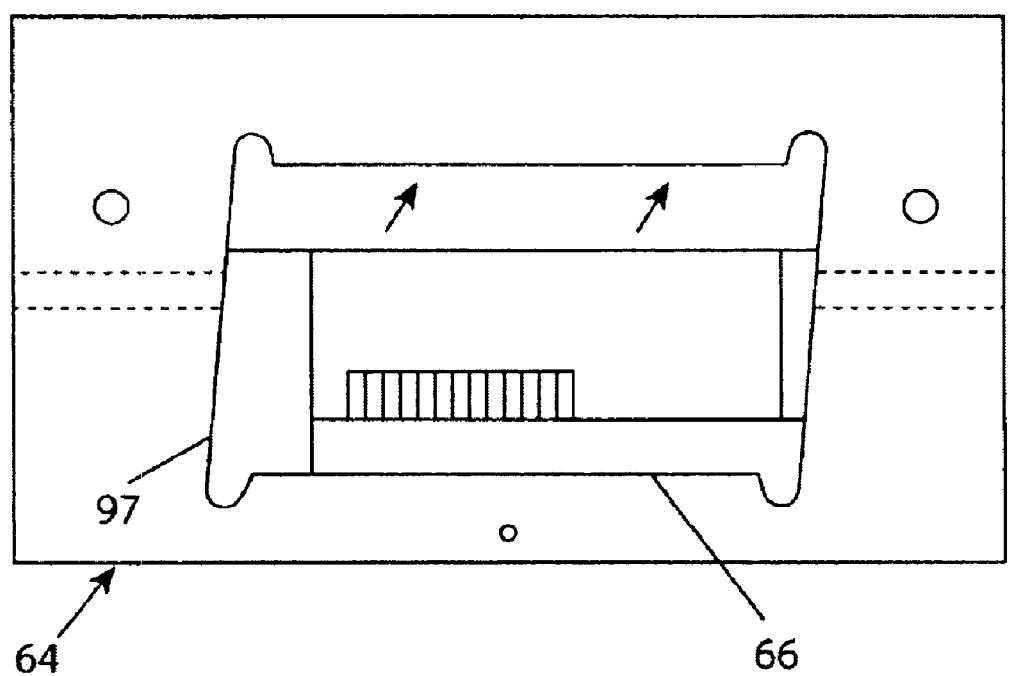
FIG. 15 depicts the blade assembly placement and upward movement in relation to the cutting template.

As shown in FIG. 13, the tamp 101 is placed on the cutting bed 56 positioning the suture 6 in vice 63 which is tightened and the tamp is then removed. Cutting template 64 is then placed onto cutting bed 56.

In the cutting method of suture 6, blade assembly 66 is placed onto cutting bed 56. The blade assembly is pressed down while slid from the top of the cutting template to the bottom along path 97. The blade depth is set to produce the desired depth of the barb. After blade assembly 66 stops at the bottom of cutting template 64, the blade assembly is removed.

Blade assembly 66 is then rotated 180 degrees and placed onto cutting bed 56. The left and top of the blade assembly are in contact with the right and bottom of the cutting template along path 97. The blade assembly is pressed down while the blade assembly is slid from the bottom to the top.

After the blade assembly 66 stops at the top of cutting template 64, the blade assembly and the template are removed.

As the process proceeds, suture 6 is rotated. The suture should be set securely in the opening of cutting bed vise 63 and previously cut barbs should not project and the process is repeated. For three sets of barbs the suture is rotated three times, for two sets, two times.

Figure 16A:
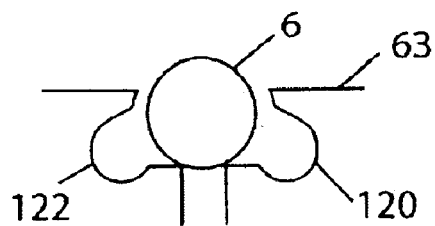
FIG. 16 is a front view depicting the setting of barbs in the cutting bed vise before and after cut using the 120 degree rotation method of cutting.
Figure 16B:
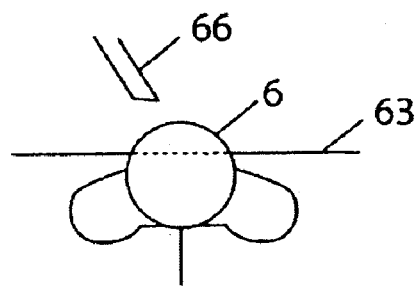
Figure 16C:
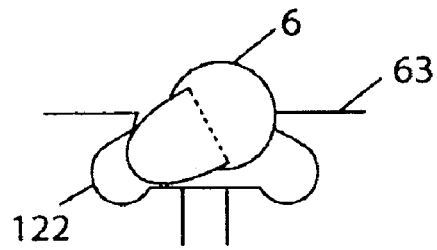
Figure 16D:
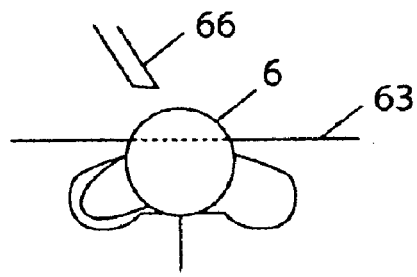
Figure 16E:
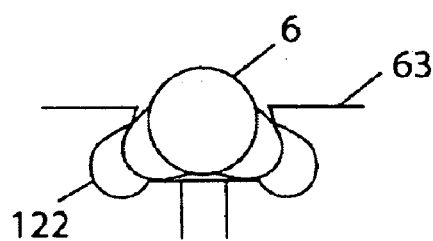
Figure 16F:
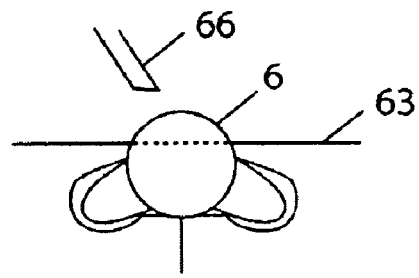

FIGS. 16A–F shows the setting of the barbs in vise 63 before and after cut. FIG. 16A shows the vise open, suture 6 uncut, with vise notches 120, 122 unused. FIG. 16B shows the vise closed with blade assembly 66 about to cut suture 6. FIG. 16C shows the vise opened after the first set of barbs are cut and placed in notch 122. FIG. 16D shows the vise closed before blade assembly 66 engages suture 6 to cut the second set of barbs. FIG. 16E shows the vise open with two sets of barbs shown and placed in notches 120, 122. FIG. 16F shows the vise closed before blade assembly 66 engages suture element 6 for the cut. After cutting, the suture 6 is removed and examined.

In the twisting method of cutting barbs, suture 6 is set up as previously described and twisted along its axis. Depending upon the number of barbs, the material of the suture and the diameter of the suture will determine the desired number of twists. For example, it has been found that size 0, PDS-2 material requiring 2-½" of barbs would require twisting it thirty-nine times for an acceptable result.

Figure 18A:
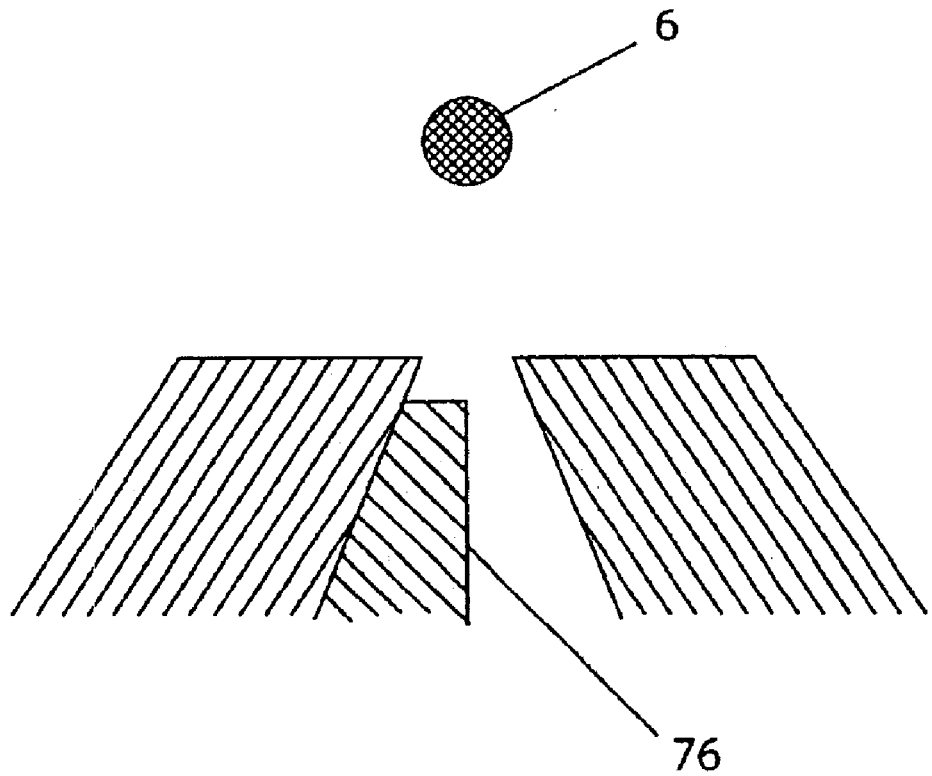
FIG. 18 is a front view depicting the setting of the suture in the cutting bed vise before cut using the twisting method of cutting.
Figure 18B:
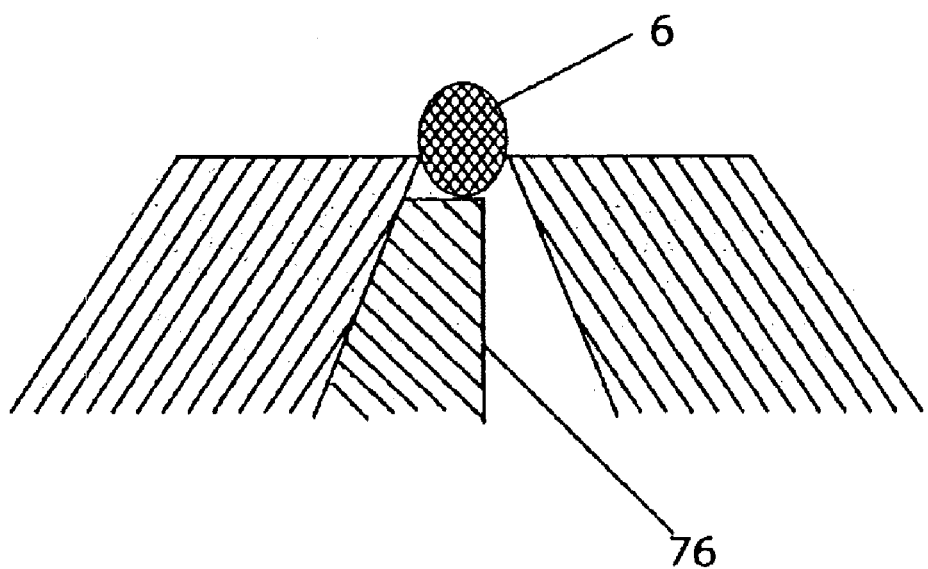

The securing of suture 6 on cutting bed 56 is, however, slightly different. In this regard, FIGS. 18A and B show the setting of suture 6 in clamp 76 before and during cut. FIG. 18A shows suture 6 being placed in the vise prior to clamping with FIG. 18B showing it post clamping. The lightly clamped suture 6 forms an elliptical shape and is ready to be cut.

The cutting method of suture 6 would be the same as that aforediscussed without, however, the need for the suture to be rotated.

Figure 19A:
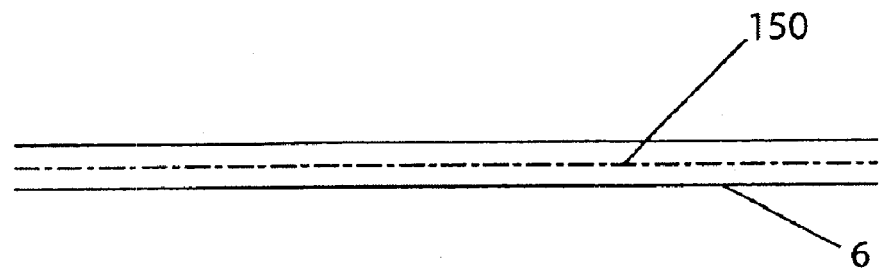
FIG. 19 depicts the various conditions of a suture before and after the twisting method of cutting.
Figure 19B:
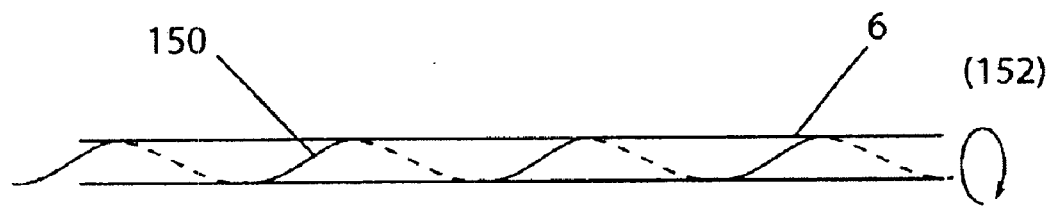
Figure 19C:
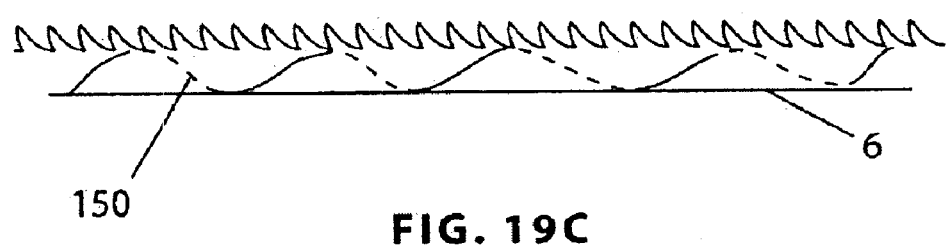

FIGS. 19A–D show the various conditions of suture 6 using the twisting method of cutting. In FIG. 19A the suture 6 is shown unmodified, with an imaginary line 150 shown to depict the longitudinal axis of it. In FIG. 19B it shows the suture 6 as it is twisted in direction (152) in preparation for cutting. FIG. 19C shows barbs cut in the twisted condition, with barbs cut along one side thereof. After the suture 6 has been cut and allowed to return to its untwisted condition, the barbs are such as those shown in FIG. 19D where the barbs spiral around the circumference of suture.

Figure 17:
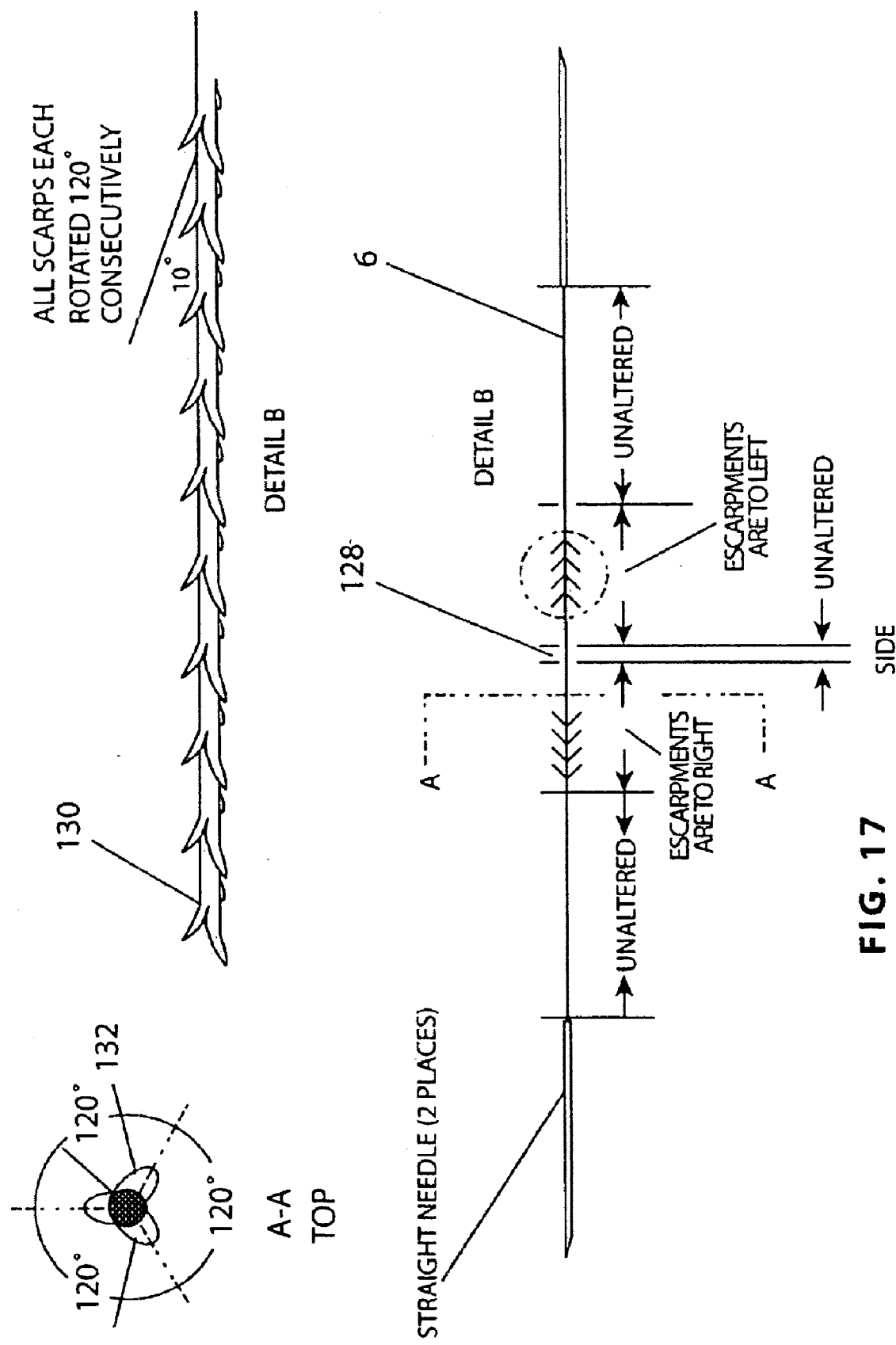
FIG. 17 is a side and top view of a barbed suture using the 120 degree rotation method of cutting.
Figure 19D:
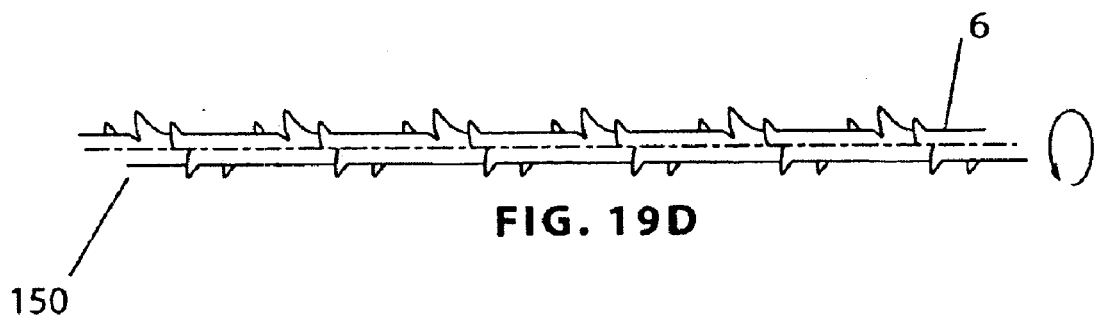

The difference in the placement of the barbs in the twisted versus the untwisted method can best be seen by comparing FIG. 17 to FIG. 19D. In FIG. 17 the suture 6 cut in the untwisted state is shown with spaced barbs at 120° about the circumference of the suture 6. In FIG. 19D the suture 6 was cut in the twisted state and upon detwisting the pattern of the barbs takes on a spiral configuration along the length of the suture 6.

Note that by omitting cutting motions when suture 6 is cut in either a twisted or untwisted state the barbs can be in a random configuration on the exterior of the suture. Also, the suture may be cut in both a twisted and untwisted state to produce other types of random configurations of barbs.

While the invention has been described in connection with what is considered to be the most practical and preferred embodiment, it should be understood that this invention is not to be limited to the disclosed embodiment, but on the contrary, is intended to cover various modifications and equivalent arrangements included within the spirit and scope of the appended claims.

What is claimed is:

1. A method of cutting barbs on a suture having a longitudinal axis, said method comprising the steps of:
   providing a suture;
   providing a cutting blade;
   twisting said suture along a y-axis prior to cutting;
   creating a barb on said suture by the motion of the blade which takes into account a cutting action by the blade on the suture in three dimensions along x-y-z axes of the suture caused by blade geometry in conjunction with blade motion; and
   providing a means for moving the blade to cause said cutting action to create the barb.

2. The method as described in claim 1 wherein the blade geometry causes a cutting action on the suture along two axes with the motion of the blade causing a cutting action along the remaining axis.

3. The method as described in claim 2 wherein the y-axis is a longitudinal axis of the suture, the x-axis is perpendicular to the longitudinal axis and the z-axis is at 90° with respect to the x-axis.

4. The method as described in claim 3 wherein the blade geometry causes a cutting action along the y and z axis with the blade motion causing a cutting action along the x-axis.

5. The method as described in claim 4 which includes providing a plurality of blades each of which creates a respective barb on the suture.

6. The method as described in claim 1 wherein the blade geometry causes a cutting action on the suture along one axis with the motion of the blade causing cutting along the remaining two axes.

7. The method as described in claim 6 wherein the y-axis is a longitudinal axis of the suture, the x-axis is perpendicular to the longitudinal axis and the z-axis is at 90° with respect to the x-axis.

8. The method as described in claim 7 wherein the blade geometry causes a cutting action along the z-axis with the blade motion causing a cutting action along the x and y axes.

9. The method as described in claim 8 which includes providing a plurality of blades each of which creates a respective barb on the suture.

10. The method as described in claim 1 wherein they-axis is a longitudinal axis of the suture, the x-axis is perpendicular to the longitudinal axis and the z-axis is at 90° with respect to the x-axis.

11. The method as described in claim 1, further comprising a step of providing a securing means for securing the suture for cutting.

12. The method as described in claim 11, wherein said securing means provides for relative rotation as between the suture and the cutting blade.

13. A method of cutting barbs on a suture having a longitudinal axis, said method comprising the steps of:
providing a suture:
providing a cutting blade;
creating a barb on said suture by the motion of the blade which takes into account a cutting action by the blade on the suture in three dimensions alone x-y-z axes of the suture; and
providing a means for moving the blade to cause said cutting action to create the barb,
wherein the motion of the blade causes cutting along the x-y-z axes.

14. The method as described in claim 13 which includes providing a plurality of blades each of which creates a respective barb on the suture.

15. The method as described in claim 14 which includes the further step of twisting said suture along the y-axis prior to cutting.

16. An apparatus for cutting barbs on a suture comprising:
a cutting bed on which a suture is maintained in place, said suture having x-y-z axes wherein the y-axis is a longitudinal axis of the suture, the x-axis is perpendicular to the longitudinal axis and the z-axis is at 90° with respect to the x-axis;
means for causing a blade assembly to contact the suture in a predetermined manner; and
said blade assembly comprising a plurality of cutting blades having a geometry, and means for moving said cutting blades along the x-axis of the suture at a plurality of locations with the movement of the blades and the blades' geometry, producing a plurality of barbs on said suture, wherein the blade geometry causes a cutting action on the suture along two axes with the motion of the blade causing a cutting action along the remaining axis.

17. An apparatus for cutting barbs on a suture according to comprising:
a cutting bed on which a suture is maintained in place, said suture having x-y-z axes wherein the y-axis is a longitudinal axis of the suture, the x-axis is perpendicular to the longitudinal axis and the z-axis is at 90° with respect to the x-axis;
means for twisting said suture along a y-axis prior to cutting;
means for causing a blade assembly to contact the suture in a predetermined manner; and
said blade assembly comprising a plurality of cutting blades having a geometry, and means for moving said cutting blades along the x-axis of the suture at a plurality of locations with the movement of the blades and the blades' geometry, producing a plurality of barbs on said suture.

18. An apparatus for cutting barbs on a suture comprising:
a cutting bed on which a suture is maintained in place, said suture having x-y-z axes wherein the y-axis is a longitudinal axis of the suture, the x-axis is perpendicular to the longitudinal axis and the z-axis is at 90° with respect to the x-axis;
means for causing a blade assembly to contact the suture in a predetermined manner; and
said blade assembly comprising a plurality of cutting blades having a geometry, and means for moving said cutting blades in the x and y axes of the suture at a plurality of locations with the movement of the blades and the blades' geometry, producing a plurality of barbs on said suture, wherein the blade geometry causes a cutting action on the suture alone two axes with the motion of the blade causing a cutting action along the remaining axis.

19. An apparatus for cutting barbs on a suture comprising:
a cutting bed on which a suture is maintained in place, said suture having x-y-z axes wherein the y-axis is a longitudinal axis of the suture, the x-axis is perpendicular to the longitudinal axis and the z-axis is at 90° with respect to the x-axis;
means for twisting said suture along a y-axis prior to cutting;
means for causing a blade assembly to contact the suture in a predetermined manner; and
said blade assembly comprising a plurality of cutting blades having a geometry, and means for moving said cutting blades in the x and y axes of the suture at a plurality of locations with the movement of the blades and the blades' geometry, producing a plurality of barbs on said suture.

20. An apparatus for cutting barbs on a suture comprising:
a cutting bed on which a suture is maintained in place, said suture having x-y-z axes wherein the y-axis is a longitudinal axis of the suture, the x-axis is perpendicular to the longitudinal axis and the z-axis is at 90° with respect to the x-axis;
means for causing a blade assembly to contact the suture in a predetermined manner; and
said blade assembly comprising a plurality of cutting blades and means for moving said cutting blades in the x and y and z axes of the suture at a plurality of locations with the movement of the blades, producing a plurality of barbs on said suture, wherein the blade geometry causes a cutting action on the suture along two axes with the motion of the blade causing a cutting action along the remaining axis.

21. An apparatus for cutting barbs on a suture comprising:
a cutting bed on which a suture is maintained in place, said suture having x-y-z axes wherein the y-axis is a longitudinal axis of the suture, the x-axis is perpendicular to the longitudinal axis and the z-axis is at 90° with respect to the x-axis;
means for twisting said suture alone a y-axis prior to cutting;
means for causing a blade assembly to contact the suture in a predetermined manner; and
said blade assembly comprising a plurality of cutting blades having a geometry, and means for moving said cutting blades in the x and y and z axes of the suture at a plurality of locations with the movement of the blades, producing a plurality of barbs on said suture.

22. A method of cutting a barb on a suture, said method comprising the steps of:
providing a suture having a longitudinal axis;
twisting said suture along its longitudinal axis; and
cutting a barb on said suture when in its twisted state.

23. The method in accordance with claim 22 which includes the further step of cutting a plurality of barbs on said suture when in its twisted state.

24. A method of cutting barbs on a suture having a longitudinal axis, said method comprising the steps of:
providing a suture;

providing a cutting blade;

creating a barb on said suture by a motion of the blade which takes into account a cutting action by the blade on the suture in three dimensions along x-y-z axes of the suture caused by blade geometry in conjunction with blade motion; and providing a means for moving the blade to cause said cutting action to create the barb, wherein the blade geometry causes a cutting action on the suture along two axes with the motion of the blade causing a cutting action along the remaining axis.

25. The method as described in claim 24 wherein the y-axis is a longitudinal axis of the suture, the x-axis is perpendicular to the longitudinal axis and the z-axis is at 90° with respect to the x-axis.

26. The method as described in claim 25 wherein the blade geometry causes a cutting action along the y and z axis with the blade motion causing a cutting action along the x-axis.

27. The method as described in claim 26 which includes providing a plurality of blades each of which creates a respective barb on the suture.

28. The method as described in claim 27 which includes the further step of twisting said suture along the y-axis prior to cutting.

29. The method of claim 28 further comprising the step of providing a securing means for securing the suture for cutting, wherein said securing means provides for relative rotation as between the suture and the cutting blade.

* * * * *

UNITED STATES PATENT AND TRADEMARK OFFICE
CERTIFICATE OF CORRECTION

PATENT NO. : 6,848,152 B2
DATED : February 1, 2005
INVENTOR(S) : Perry Genova, Robert C. Williams, III and Warren Jewett It is certified that error appears in the above-identified patent and that said Letters Patent is hereby corrected as shown below:

Column 8,
Line 61, please change "they-axis" to -- the y-axis --.

Column 9,
Lines 40-41, please delete "according to".

Column 10,
Line 5, please change "alone two axes" to -- along two axes --

Signed and Sealed this

Twenty-fourth Day of May, 2005

JON W. DUDAS
*Director of the United States Patent and Trademark Office*